US006376745B1

US 6,376,745 B1

(12) United States Patent
Atabekov et al.

(10) Patent No.: US 6,376,745 B1
(45) Date of Patent: Apr. 23, 2002

(54) METHODS FOR COEXPRESSION OF MORE THAN ONE GENE USING AT LEAST ONE INTERNAL RIBOSOME ENTRY SITE (IRES)

(76) Inventors: Joseph Atabekov, Lomonosovski prospekt 15-142, Moscow 117311 (RU); Timo Korpela, Kasarminkatu 5 as 8, FIN-20500, Turku (FI); Yurii Dorokhov, Profsojuznaja Street 146-3-187, Moscow 117321 (RU); Peter Ivanov, Vavilova Street 37A-18, Moscow 117312 (RU); Maxim Skulachev, Moscow State University, M-176, Moscow 117234 (RU); Nina Rodionova, Ramenski Street 19-184, Moscow 117607 (RU); Olga Karpova, Garibaldy Street 15-1-50, Moscow 117335 (RU)

( * ) Notice: Subject to any disclaimer, the term of this patent is extended or adjusted under 35 U.S.C. 154(b) by 0 days.

(21) Appl. No.: 09/424,793

(22) PCT Filed: May 29, 1998

(86) PCT No.: PCT/FI98/00457

§ 371 Date: Feb. 8, 2000

§ 102(e) Date: Feb. 8, 2000

(87) PCT Pub. No.: WO98/54342

PCT Pub. Date: Dec. 3, 1998

(30) Foreign Application Priority Data

May 30, 1997 (FI) .................................................. 972293

(51) Int. Cl.[7] .................... C12N 15/82; C12N 15/63; A61K 35/00; A01H 5/00; C07H 21/02
(52) U.S. Cl. .................... 800/278; 435/320.1; 435/414; 435/419; 424/93.21; 536/23.1; 800/317.3
(58) Field of Search ................ 536/23.1; 435/325, 435/320.1, 414, 419; 800/287, 288, 295, 317.3, 278; 424/93.21

(56) References Cited

FOREIGN PATENT DOCUMENTS

| EP | 0672754 | 9/1995 |
|----|---------|--------|
| GB | 2262099 | 6/1993 |
| WO | WO 9514775 | 6/1995 |
| WO | WO 9612028 | 4/1996 |
| WO | WO96 27676 | 9/1996 |
| WO | WO 9633272 | 10/1996 |
| WO | WO97 14809 | 4/1997 |

OTHER PUBLICATIONS

Kaminski and Jackson (1995) RNA 1:985–1000.*
Basso, J et al (1994) J Gen Virol 75:3157–3165.*

(List continued on next page.)

Primary Examiner—James Ketter
Assistant Examiner—Christopher Drabik
(74) Attorney, Agent, or Firm—Birch, Stewart, Kolasch & Birch, LLP.

(57) ABSTRACT

The present invention is drawn to a recombinant nucleic acid having (a) a transcriptional promoter; (b) a first plant-expressible structural gene linked to the transcriptional promoter, (c) a cDNA sequence element having an internal ribosome entry site of tobamovirus moving protein (MP) gene ($IRES_{mp}$) which is located 3' to the first plant-expressible structural gene, and (d) a second plant-expressible gene located 3' to the ($IRES_{mp}$) such that the second gene is placed under the translational control of ($IRES_{mp}$); wherein the first plant-expressible gene, ($IRES_{mp}$) and the second plant-expressible gene are transcribed under the action of the transcriptional promoter to give a primary transcript, and the first plant expressible gene of the primary transcript is able to translate by ribosome scanning mechanism and the second plant expressible gene of the primary transcript is capable of translation under the action of ($IRES_{MP}$). The present invention is further drawn to a method of simultaneously expressing desired genes in vitro and in planta by using crTMV RNA sequences upstream or the MP gene, i.e. $IRES_{mp}$.

10 Claims, 5 Drawing Sheets

OTHER PUBLICATIONS

Thomas et al (1991) Journal of Virology 65:2953–2959.*
Belsham et al (1991)J Gen Virol 72:3109–3113.*
(Urwin, P et al 2000 Plant Journal 24(5), 583–589.*
Aran et al (1994) Proc Nat'l Acad Sci, USA 91:3176–3180.*
V. Gurtu et al., Biochem. and Biophys. Res. Comm., vol. 229, pp. 295–298 (1996) (Article No. 1795).
Virology, vol. 232, 1997, P.A. Ivanov et al., p. 32–p. 43.

Journal of General Virology, vol. 75, 1994, Johnny Basso et al., pp. 3157 –p. 3165.
Bio/Technology, vol. 12, Jul. 1994, Yoshikazu Sugimoto et al., p. 694–p. 698.
Nucleic Acids Research, vol. 19, No. 16, 1991, Randal J. Kaufmann et al., p. 4485–p. 4490.

* cited by examiner

METHODS FOR COEXPRESSION OF MORE THAN ONE GENE USING AT LEAST ONE INTERNAL RIBOSOME ENTRY SITE (IRES)

This application is the national phase under 35 U.S.C. §371 of PCT International Application No. PCT/FI98/00457 which has an International filing date of May 29, 1998, which designated the United States of America.

FIELD OF INVENTION

This invention relates to plant molecular biology in general, and in particular, to nucleic acid sequences which regulate the internal and 3'-proximal gene expression in polycistronic mRNA transcripts. This invention will enable the control of transgene expression through the generation of polycistronic fusion mRNAs in which all the genes are translationally active due to the presence of the IRESmp element(s).

BACKGROUND OF THE INVENTION

According to the ribosome scanning model, traditional for most eukaryotic mRNA, the 40S ribosomal subunit binds to the 5'-cap and moves along the nontranslated 5'-sequence until it reaches an AUG codon (Kozak (1986) Adv.Virus Res. 31:229–292; Kozak (1989) J.Mol.Biol. 108: 229–241). Although for the majority of eukaryotic mRNAs only the first open reading frame (ORF) is translationally active, there are different mechanisms by which mRNA may function polycistronically (Kozak (1986) Adv.Virus Res. 31:229–292). If the the first AUG has unfavorable sequence context, 40S subunits may bypass it and initiate at downstream AUG codon (leaky scanning mechanism). Termination-reinitiation has also been suggested to explain the initiation of translation of functionally dicistronic eukaryotic mRNAs (Kozak (1989) J.Mol.Biol. 108: 229–241). Another mechanism for discontinuous ribosome migration ("shunting") on mRNA has been recently proposed for cauliflower mosaic virus (CaMV) 35S RNA (Futerrer et al.(1993) Cell 73: 789–802).

In contrast to the majority of eukaryotic mRNAs, the initiation of translation of picornavirus RNAs takes place by an alternative mechanism of internal ribosome entry. A picornaviral 5'-nontranslated region (5'NTR) contains a so-called internal ribosome entry site (IRES) or ribosome landing pad (Pelletier and Sonennberg (1988) Nature 334: 320–325; Molla. et al. (1992) Nature 356; 255–257) which is folded into a complex secondary structure and contains a pyrimidine-rich tract followed by an AUG codon (Agol (1991) Adv.Virus Res. 40: 103–180; Wimmer et al. (1993) Annu.Rev.Genet.27: 353–436; Sonennberg and Pelletier (1989) BioEssays 11: 128–132). Internal ribosome entry has also been reported for other viral (Le et al. (1994) Virology 198: 405–411; Gramstat et al. (1994) Nucleic Acid Res. 22: 3911–3917) and cellular (Oh et al. (1992) Gen Dev. 6: 1643–1653) RNAs.

It is important to emphasize that the picornavirus and other known IRESes are not active in the plant cell systems.

The genome of tobamoviruses (TMV UI is the type member) contains four large ORFs. In vitro translational experiments have shown that the two components of the replicase (the 130K and its read-through 183K proteins) are translated directly from the genomic RNA (Pelham and Jackson (1976) Eur.J.Biochem 67: 247–256). The other two proteins (30K movement protein, MP, and coat protein, CP) are translated from two individual subgenomic RNAs (sgRNAs). Two structurally dicistronic I$_2$ sgRNA is translated to give the 30K MP, while its 3'-terminal CP gene is silent and a monocistronic sgRNA codes the CP (Palukaitis and Zaitlin (1986) in The Plant Viruses, eds. Van Regenmortel and M.Fraenkel-Conrat, 2: 105–131, Plenum Press).

Recently a new tobamovirus, crTMV, has been isolated from Oleracia officinalis L. plants and the genome has been sequenced (6312 nucleotides) (Dorokhov et al. (1993) Doklady of Russian Academy of Sciences 332: 518–522; Dorokhov et al. (1994) FEBS Lett. 350: 5–8). A peculiar feature of crTMV is its ability to infect systemically the members of Cruciferae family. The crTMV RNA contains four ORFs encoding the proteins of 122K (ORF1), 178K (ORF2), the read through product of 122K, 30K MP (ORF3) and 17K CP (ORF4). Unlike other tobamoviruses, the coding regions of the MP and CP genes of crTMV overlap for 25 codons, i.e. 5' of the CP coding region are sequences encoding MP.

It has been shown that unlike the RNA of typical tobamoviruses, translation of the 3'-proximal CP gene of crTMV RNA occurs in vitro and in planta by mechanism of internal ribosome entry which is mediated by a specific sequence element, IREScp (Ivanov et al. (1997) Virology 231, in press). In that work three types of synthetic dicistronic RNA transcripts were constructed and translated in vitro: (i) "MP-CP-3'NTR" transcripts contained MP gene, CP gene and the 3'-nontranslated region (NTR) of crTMV. These constructs were structurally equivalent to dicistronic subgenomic RNAs produced by tobamoviruses in vivo. (ii) "ΔNPT-CP" transcripts contained partially truncated neomycine phosphotransferase I gene and CP gene. (iii) "CP-GUS" transcripts contained the first CP gene and the gene of E.coli (β-glucuronidase (GUS) at the 3'-proximal position.

The results indicated that the 148-nt region upstream of the CP gene of crTMV RNA contained IREScp promoting internal initiation of translation in vitro. Dicistronic IREScp containing chimeric mRNAs with the 5'-terminal stem-loop structure preventing translation of the first gene (MP, ΔNPT or CP), expressed the CP or GUS genes despite their 3'-proximal localization. The capacity of crTMV IREScp for mediating internal translation distinguishes this tobamovirus from the well known type member of the genus, TMV UI. The equivalent 148-nt sequence from TMV RNA was uncapable of mediating internal translation. Two mutants were used to study structural elements of IREScp. It was concluded that integrity of IREScp was essential for internal initiation. The RNA analysis of IREScp revealed the polypurine-rich stretch and stem-loop structure.

The crTMV provides a new example of internal initiation of translation, which is markedly distinct from IRESes shown for picornaviruses and other viral and eukaryotic mRNAs.

In order to show that the IREScp is active not only in vitro, but also in vivo two approaches were used: i) constructing of the transgenic rapeseed plants (Brassica napus L.) containing in its genome the crTMV cDNA including MP, CP genes and 3'NTR; ii) the particle gun bombardment of tobacco plant leaves with the cDNA construct "CP-IREScp-GUS" under the control of CaMV 35S promoter and terminator. Both approaches show that IREScp is active in plants (Ivanov et al., results not published).

SUMMARY OF THE INVENTION

A primary object of this invention is to provide a method which will enable to express simultaneously desired genes in vitro and in planta. This object is to be accomplished by utilising crTMV RNA sequences upstream of MP gene is termed here as IRESmp. The method of this invention involves the construction of recombinant DNA molecule which comprises of a transcriptional promoter, the first plant-exspressible gene linked to the said transcriptional promoter, IRESmp located 3' to the first gene and the second plant-expressible gene located 3' to IRESmp such that the second gene is placed under the translational control of IRESmp. The primary chimeric continuous RNA transcript in positive sense polarity is produced by the transformed cells from plant-expressible promoter. The expression of the first gene takes place by direct translation of the 5'-proximal gene of this mRNA but the translation of the 5'-distal gene of dicistronic mRNA will be promoted by IRESmp.

BRIEF DESCRIPTION OF THE FIGURES

FIGS. 3a–3f is a schematic representation of the di- and monocistronic transcripts; (a) HCPUIspmpGUS, the 5'-proximal crTMV CP gene with upstream sequence forming a potentially stable hairpin (H) and GUS gene separated by the 228-nt region upstream of TMV UI MP gene (UIspmp); (b) HCPIREScpGUS, the 148-nt region upstream of crTMV CP gene (IREScp) inserted as the intercistronic spacer, (c) the 228-nt region upstream of crTMV MP gene (IRESmp) inserted as the intercistronic spacer, (d) monocistronic IRESmpGUS, GUS gene with IRESmp as being the leader; (e) monocistronic αβGUS, αβ translational enhancer of PVX genomic RNA as leader, (f) the nucleotide sequence (SEQ ID NO:2) and putative secondary structure of hairpin (H) upstream of CP gene in transcripts (a–c).

DETAILED DESCRIPTION OF THE INVENTION

The following difinitions are provided to remove ambiguities in the intent or scope of their usage. Expression refers to the transcription and translation of gene so that a protein is synthesized. Promoters refers to the sequence at the 5'-end of the first gene which dirts the initiation of DNA transcription. Promoter sequences are necessary to drive the expression of the downstream gene(s). Eukaryotic (including plant-specific) promoters generally contain the TATA box about 10–35 bp 5' to the transcription start site. 35S promoter refers to a plant-expressible cauliflower mosaic virus promoter providing the TATA box and other sequences responsible for maximum efficiency of transcription. This promoter could also serve as a transcriptional recombinant promoter for gene expression in monocotyledonous plants (Last et al., European Patent Application number: 91304205.7) and plant anaerobic regulatory element (Peacock et al., European Patent Application number: 88300852.6). IRESmp refers to the sequence upstream of crTMV MP gene.

Figure 1:
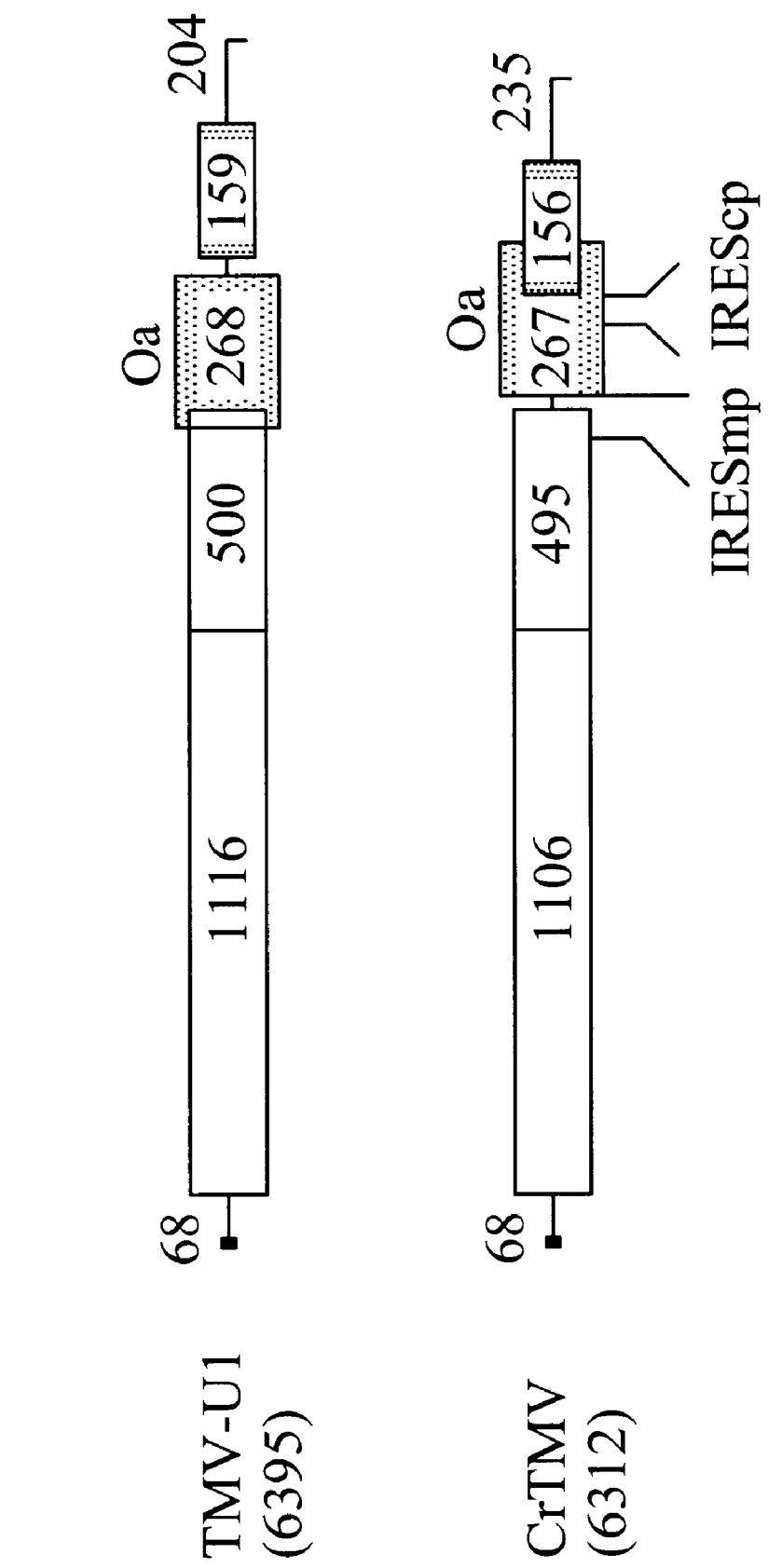
FIG. 1 shows the genetic maps of TMV UI and crTMV. The location of IRESmp and IREScp on crTMV genetic map is indicated.
Figure 2:
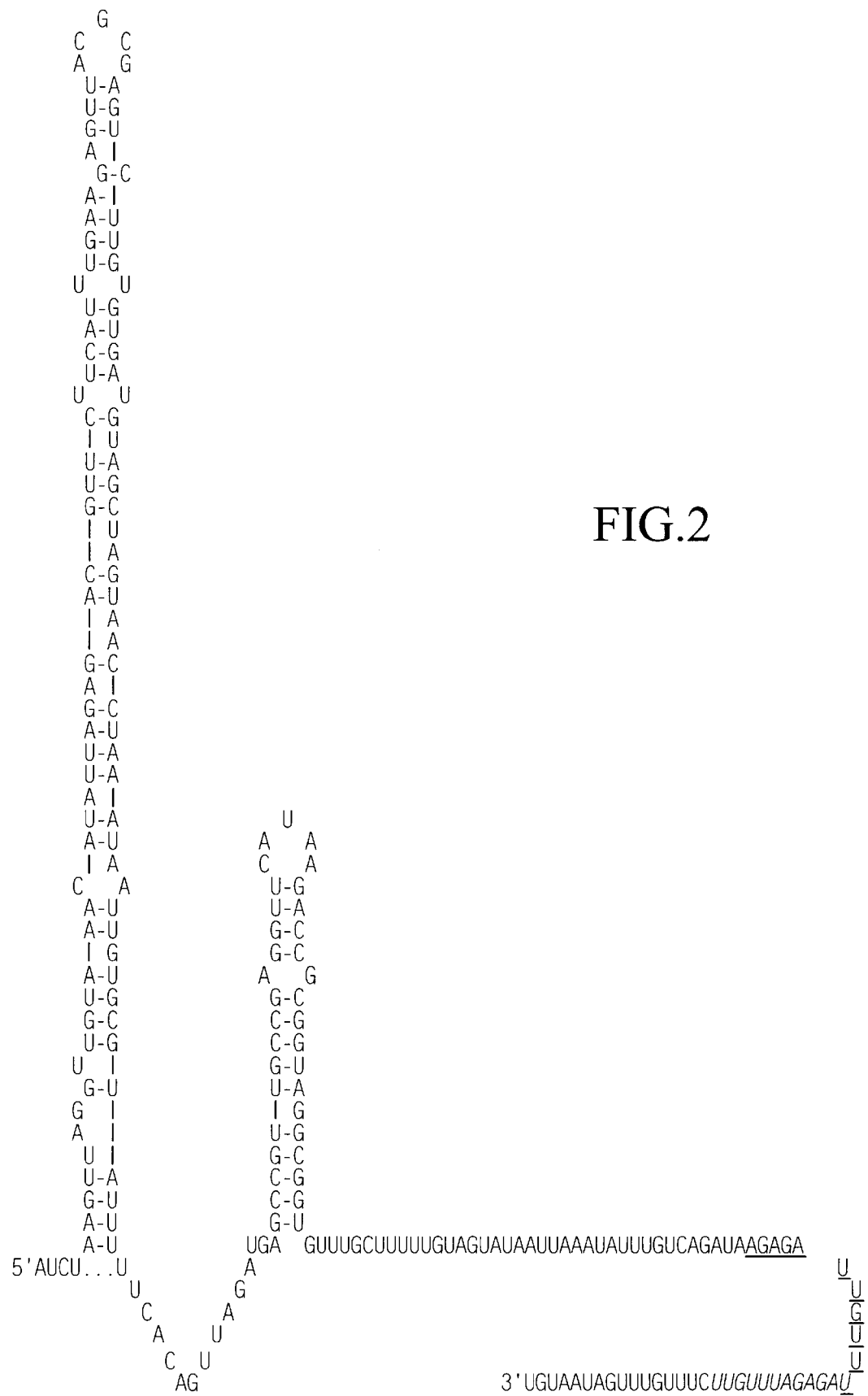
FIG. 2 shows the nucleotide sequence (SEQ. ID NO:1) and proposed secondary structure of 227-nt IRESmp containing region of crTMV RNA upstream of the MP gene AUG codon (in bolt).

A primary objective of this invention is to provide a method which will enable those skilled in the art to express simultaneously desired genes in vitro, in animal and in planta. This object is to be accomplished by utilising crTMV RNA sequences upstream of MP gene which we have termed IRESmp (FIGS. 1 and 2) in contrary to earlier described IREScp (FIG. 1). It has been found that the 228-nt region upstream of crTMV RNA MP gene contains IRESmp (FIGS. 1 and 2). This IRES element functions in chimeric bicistronic transcripts and provides expression of 3'-proximal genes in vitro (plant and animal protein synthesizing systems) and in planta.

The IRES elements can be used in transgenic expression constructs to circumvent the constraints of cap-mediated translation and to create polyfunctional RNAs:

a) coexpression of defined gene products in cell culture and transgenic plants and animals. Many in vitro applications for plant and mammalian transgenesis demand the coexpression of heterologous gene products. For example, in order to establish stable cell clones and lines of transgenic plants and animals producing a recombinant protein it is generally necessary to introduce vectors for expression both the protein of interest and the selectable marker. This is usually achieved either by co-transfecting cells with two independent constructs or by introducing a single vector harbouring two discrete expression cassettes. The first approach is often limited by the inefficiency of co-transfection. The second one requires the construction of relatively complex vectors and generally suffers from unreliable and/or low expression of the nonselectable cDNA. The use of an IRES in dicistronic expression vectors can circumvent these problems by enabling a single transcription unit to provide efficient production of both the protein of interest and a selectable marker (Kaufman et al. (1991) Nucleic Acids Res.19: 4485–4490; Ghattas et al. (1991) Mol.Cell.Biol. 11: 5848–5859; Sugimoto et al., (1994) Biotechnology 12: 694–698);

b) Functional expression cloning of novel cDNAs. In addition to facilitating the stable expression of characterized cDNAs, vectors incorporating IRES-mediated coexpression of a selectable marker may also be applied to the isolation of new genes through functional cloning approaches. For instance, one route to the identification of cDNAs that affect the growth or differentiation of a particular cell type is to screen populations of cells transfected with cDNA expression libraries. Vectors with IRES-linked gene expression of a selectable marker promise significant increases in efficiendy by ensuring that the majority of selected transfectants also express cDNA. A powerful strategy for cloning cDNAs that encode interacting proteins is the two-hybrid system (Fields and Song (1989) Nature 340: 245–246). This screen is based on the coexpression of a hybrid between a cDNA and an activation domain along with a fusion protein of DNA binding domain and a target protein. The requirement for production of two proteins suggests that the methodology could be simplified by incorporating an IRES element to produce a single vector for coexpression of both fusion proteins. Certain IRES sequences have recently been demonstrated to work in Saccharomyces cerevisiae (Iisuka et al. (1994) Mol.Cell.Biol. 14:7322–7330), so this approach could be applicable in yeast as well as in analogous mammalian systems (Vasavada et al. (1991) Proc. Natl Acad.Sci. USA 88: 10686–10690; Fearon et al. (1992) ibid 89: 7958–7962).

It has been shown that crTMV RNA IREScp functions in bicistonic transcripts in vitro (Ivanov et al (1997), in press) and in planta (Ivanov et al., results not published). The present invention provides the first proof that the nucleotide sequence region upstream of crTMV MP gene is IRESmp which is more active in chimeric bicistronic transcripts in vitro than an IREScp element. The DNA sequences, DNA fragments containing an IRESmp element and constructions of the present invention will enable to express reporter genes in vitro and in planta.

The method of this invention involves the construction of recombinant DNA molecule which comprises of plant-expressible structural gene, IRESmp and plant-expressible reporter gene, the plant-expressible reporter gene being located 3' to the IRESmp and positioned such that expression of the reporter gene is controlled by IRESmp. The recombinant DNA molecule may be incorporated into DNA construct or vector in combination with suitable regulatory sequences (promoter, terminator, enhancer, transit peptide etc). The transit peptide may be homologous or heterologous to reporter protein and will be chosen to ensure secretion to the desired organelle or extracellular space. Such a DNA construct may be cloned or transformed into a biological system which allows expression of the reporter protein. Suitable biological systems include yeast; viruses; cultured cells (such as insect cells, mammalian cells and plant cells) and animals and plants.

The seconde objective of this invention is to provide simultaneous expression of plant virus-derived genes (replicase, MP and CP genes) using IRESmp and IREScp, for example, in the following DNA expressing cassettes: replicase gene/IRESmp/MP gene/IREScp/CP gene. It is well known that the transgenic plants containing in its genome plant virus-derived genes are resistant to homologous plant viruses. It is possible to create transgenic plants resistant to different plant viruses using such DNA construction. The DNA expressing cassettes may be incorporated into a DNA construct or vector in combination with suitable regulatory sequences (promoter, terminator, transit peptide, enhancer etc). The DNA sequence may be placed under the control of a homologous or heterologous promoter which may be a constitutive or an inducible promoter (stimulated by, for example, environmental conditions, presence of a pathogen, presence of a chemical). Plant cells may be transformed with recombinant DNA consructs according to a variety of known methods (Agrobacterium Ti plasmids, electroporation, microinjection, microprojectile bombardment etc). The transformed cells may then in suitable cases be regenerated into whole plants in which the new nuclear material is stably incorporated into the genome. Both transformed monocotyledonous and dicotyledonous plant may be obtained in this way. Examples of genetically modified plants which may be produced include field crops, cereals, fruit and vegetables such as canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The third objective of this invention is to express coordinately in transgenic plants a set of genes. Coordinated expression is useful, for example, when it is necessary to express a protein consisting of various polypeptides or when several enzymes of a biosynthetic pathway must be expressed.

A further objective of this invention is to provide the simultaneous production of proteolytic enzymes to cleave a polyprotein product.

The objects of this invention are plants, plant cells and plant tissues grown in fields or is specific fermentors.

Further objects are vectors and expression cassettes comprising of IRESmp, and bacterial cells comprising such vectors suitable for maintenance, replication, and plant transformation.

It is to be notified that eukaryotic IRES sequences may be more widespread than has realized hitherto because they cannot be identified by sequence homology; known IRESes have been functionally defined and, so far, no conserved features have been found. Therefore, the present invention is not limited to any specific IRES sequence described here only. Rather this invention describes functional property of any IRESmp sequence.

The invention is further illustrated in the following non-limiting examples and with reference to the figures.

EXAMPLES

Example 1
Construction of Plasmids Containing IRES

Standard molecular biological techniques were carried out according to Maniatis et al. (1982) Molecular Cloning: a Laboratory Manual. Cold Spring Harbor Laboratory, Cold Spring Harbor, N.Y. All plasmids utilized in the invention can be prepared according to the directions of the Specification by a person of ordinary skill in the art without undue experimentation employing materials readily available in the art.

To obtain pCP, crTMV cDNA was amplified by PCR with primers which introduced KpnI site at the 5'-end and HindIII site at the 3'-end of the crTMV CP gene and the product was cloned between the KpnI and HindIII sites of pBluescript II SK+. The plasmid pHCP differs from previous construct by the presence of inverted tandem repeat (KpnI-EcoRI and ClaI-KpnI fragments from pBluescript II SK+ polylinker sequence). Cloning of the BamHI/SacI fragment from pTBSMPΔCPSma (described by Ivanov et al. (1997) Virology 231, in press) into pCP resulted in formation of pCPMP. This plasmid contains crTMV CP and MP genes with several restriction sites in the intercistronic area. CPIRESmpMP construct was generated by digection of the pCPMP with EcoRV and BglII followed by insertion of the EcoRV/BglII fragment, derived from pG7S3 crTMV cDNA sequenced clone. This clone contained C-terminal part of the replicase gene (EcoRI site) and the 5' terminal coding part of the MP gene (BglII site). To obtain monocistronic construct IRESmpGUS, pGEM3zf+ vector was digested with EcoRI and SalI and then ligated with two inserts: GUS-gene (NcoI/SalI fragment from pRTαβGUS described by Zelenina et al. (1992) FEBS Lett. 296. 276–270) and EcoRI/NcoI-cut PCR-product which was amplified from crTMV cDNA clone pG7S20 (Ivanov et al. (1997) Virology 231, in press) using primers which introduced EcoRI and KpnI sites at the 5'-end and NcoI site at the 3'-end of the IRESmp sequence (228 nucleotides upstream of the crTMV MP gene). The EcoRI/PstI fragment of IRESmpGUS was inserted into EcoRI/PstI-cut pHCP to give dicistronic construct pHCPIRESmpGUS. The plasmid UIspGUS was created by cloning two fragments (HindIII/NcoI-cut UIspGUS and NcoI-XbaI-cut GUS gene) between the HindIII and XbaI sites of Bluescript II SK+. UIsp was obtained in RT-PCR using genomic TMV UI RNA with 5'-oligonucleotide primer corresponding to 4676–4686 of the TMV UI cDNA containing HindIII site and the 3'-primer containing NcoI site and complementary to nucleotides 4883–4903 of the TMV UI cDNA. GUS gene was obtained by digesting pRTαβGUS plasmid with NcoI and XbaI. The HindIII/XbaI fragment of UIspGUS was cloned into HindIII/XbaI-cut pHCP to obtain pHCPUIspGUS. The creation of αβGUS was described by Ivanov et al. (1997) (Virology 231, in press).

The pFF series of constructs have 35S-enhancer, 35S-promoter and 35S-polyadenylation signal (Topfer et al. (1987) Nucleic Acids Res. 415, 5890). These plasmids were derived from pFF19 and pFF19GUS constructs described earlier (Morozov et al. (1997) J.Gen.Virol., in press). The constructs pFFCPIREScpGUS, pFFCPIRESmpGUS and pFFCPUIspmpGUS were generated by cloning KpnI/XbaI-fragments of CPIRESmpGUS and CPUIspmpGUS, respectively, into pFF19 vector.

Example 2
In vitro Transcription

The plasmids HCPIRESmpGUS, HCPIREScpGUS, HCPUIspGUS, αβGUS, UIspGUS were linearized by SacI. The recombinant plasmids were transcribed in vitro as described by Tomashevskaya et al. (1993) J.Gen.Virol. 74, 2717–2724). Agarose gel electrophoresis of RNA transcripts confirmed that they were intact. The RNA concentration was quantified by agarose gel electrophoresis and spectrophotometry.

Example 3
Cell-free Translation

In vitro translation in rabbit reticulocyte lysates (RRL) was performed as described by Pelham and Jackson (1976) (Eur.J.Biochem 67, 247–256) with minor modifications. Translation mixture (25 μl final volume) contained 10 μl nuclease-treated lysate containing 1 mM $CaCl_2$ with hemin; 20 mM Hepes, pH 7.6; 1 mM ATP; 200 mM GTP; 2.5 mM magnesium acetate; 100 mM potassium acetate; 2 mM DDT; 15 mM creatine phosphate: 1 μg creatine phosphokinase; 5 mM cAMP; 2 mM EGTA; 3 μg yeast tRNA, 125 μM of each essential amino acid excluding methionine; 800 μCi/ml [$^{35}$S]-methionine (Amersham, >1000 Ci/mmol) and 40–100 μg/ml of virus RNA. Incubation was carried out at 30° C. for 60 min. Translation in wheat germ extracts (WG) was performed according to the manufacturer's (Promega) protocol in the presence of [$^{35}$S]-methionine for 60 min at 25° C. Radiolabeled translation products were analysed by SDS-PAGE and localized by autoradiography on the dried gel.

It has long been known that only the 5'-proximal gene of tobamovirus genomic RNA can be directly translated by ribosomes. A dicistronic uncapped sgRNA called $I_2$ directs translation of only MP, while a second, capped monocistronic sgRNA directs synthesis of the CP (reviewed by Palukaitis and Zaitlin (1986) in The Plant Viruses, eds. Van Regenmortel and M. Fraenkel-Conrat, 2: 105–131, Plenum Press). Unexpectedly, our experiments have shown that, unlike TMV UI RNA, genomic RNA of crTMV tobamovirus directs synthesis of MP in vitro (data not shown).

Figure 4:
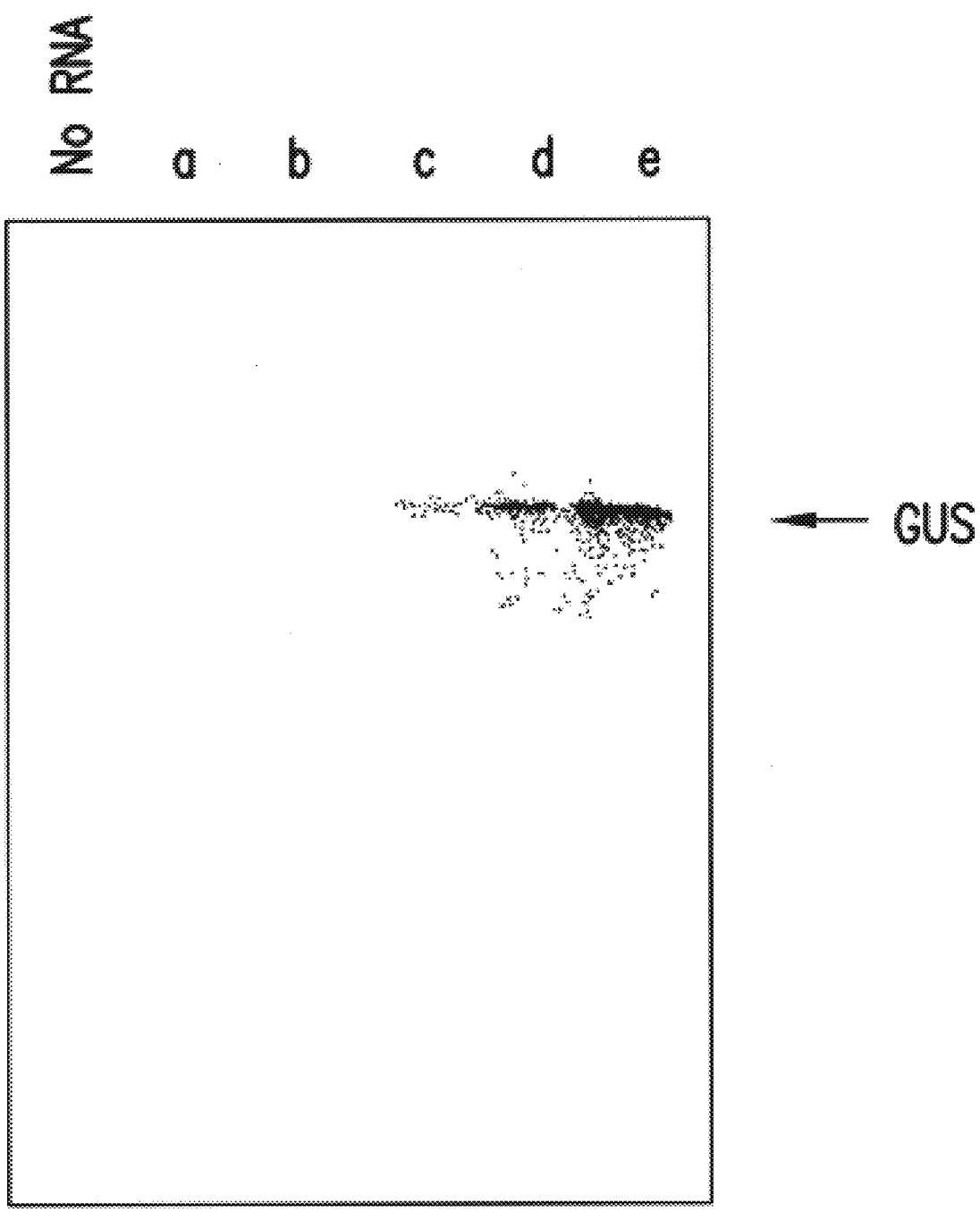
FIG. 4. Analysis of proteins directed in vitro in rabbit reticulocyte lysate (RRL) by the transcripts depicted in FIG. 3. Autoradiogram of gradient 8–20% polyacrylamide-SDS gels containing [$^{35}$S]methionine-labeled products directed by uncapped transcripts in RRL. Concentration of transcripts is 40 (μg/ml).

The question arises as to whether the MP-coding sequences immediately adjacent to IRESmp are essential for internal initiation. Therefore, chimeric mRNA (HCPIRESmpGUS in FIG. 3) containing the 3'-proximal foreign GUS gene was translated in WGE (data not shown) and RRL (FIG. 4). It was found that IRESmp of crTMV tobamovirus was efficient in mediating the 3'-proximal GUS gene expression and is more active than that is IREScp.

In order to demonstrate that IRESmp-mediated translation is unusual for tobamoviruses, the equivalent dicistronic construct (HCPUIspmpGUS in FIG. 3) was made containing the 228-nt region upstream of TMV UI MP gene as the intercistronic spacer. FIGS. 4 shows that TMV UI-derived sequence was incapable of mediating internal ribosome entry. It is important that the second ORF was translated from IREScp- and IRESmp-containing dicistronic RNA-transcripts that retained their integrity during incubation in translation extract (data not shown).

Example 4
Particle Bombardment

Particle bombardment was performed using flying disk method (for example, see Daniell (1993) (Methods in Enzymology 217, 537–557) with high-pressure helium-based apparatus PDS-1000 (Bio-Rad). Briefly, for each series of shots, DNA was precipitatd on tungsten particles with calcium chloride and ethanol after the addition, while vortexing, of 10 μl of plasmid DNA (at 0.5–1.5 mg/ml to 6 mg of tungsten particles suspended in 100 μl of 50% glycerol, and then tungsten particles kept in suspension in cold 95% ethanol (90 mg/ml). After sonication 5 μl of this mixture was placed immediately on each plastic flying disk and used for bombardment when the particles had dried. A detached leaf of *Nicotiana benthamiana* (15–30 mm size) was placed in the center of a plastic Petri dish and bombarded on a solid support at a target distance of 7 cm. Bombardment was done with a pulse of 1350 kPa helium gas in a vacuum chamber.

Inoculated leaves were sampled 24 to 72 hrs after bombardment. IRES activity was monitored by histochemical detection of GUS expression described (Jefferson (1987) Plant Molecular Biology Report 5, 387–405). Samples were infiltrated in the colorimetric GUS substrate, modified (De Block and Debrouwer (1992) Plant J. 2, 261–266) to limit the diffusion of the intermediate products of the reaction: 0.115 M phosphate buffer, pH: 7.0, containing 5-bromo-4-chloro-3-indolyl-β-D-glucuronide (X-Gluc) 600 μg/ml; 3 mM potassium ferricyanide; 10 mM EDTA. After incubation overnight at 37° C., the leaves were fixed in 70% ethanol and examined by light microscopy.

Figure 5A:
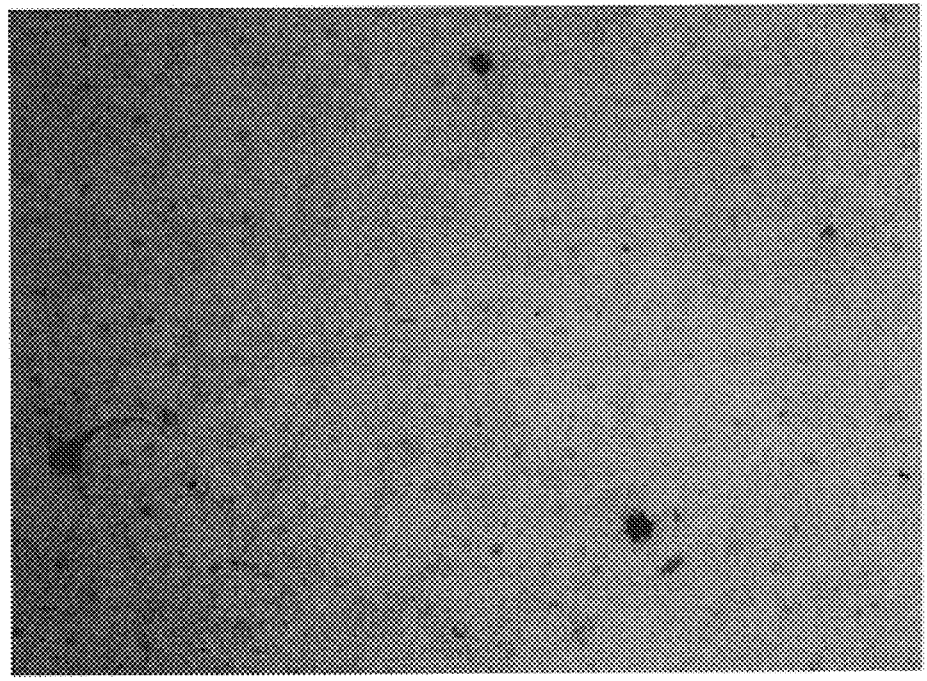
FIGS. 5A–5B. Histochemical analysis of GUS activity in leaves of Nicotiana benthamiana plants bombarded with pFFCPIREScpGUS (panel a) and pFFCPIRESmpGUS (panel b). The presence of GUS activity is indicated by the blue histochemical reaction.
Figure 5B:

FIG. 5 shows that 35S-based DNA constructs CPIREScpGUS (a) and CPIRESmpGUS (b) are active in GUS synthesis developed by histochemical reactions. The 35S-based constructs CPUIspcpGUS and CPUIspmpGUS are not active in GUS synthesis in plant leaf (Data not shown).

What is claimed is:

1. A recombinant nucleic acid comprising:
   (a) a transcriptional promoter;
   (b) a first plant-expressible gene linked to said transcriptional promoter,
   (c) a cDNA sequence element comprising an internal ribosome entry site of tobamovirus moving protein (MP) gene ($IRES_{MP}$) which is located 3' to the first plant-expressible gene, and (d) a second plant-expressible gene located 3' to the $IRES_{MP}$ such that the second gene is placed under the translational control of the $IRES_{MP}$;

wherein the first plant-expressible gene, $IRES_{MP}$ and the second plant-expressible gene are transcribed under the action of the transcriptional promoter to produce a primary transcript, and the first plant expressible gene of the primary transcript is able to translate by ribosome scanning mechanism and the second plant expressible gene of the primary transcript is capable of translation under the action of $IRES_{MP}$.

2. The nucleic acid according to claim 1, wherein at least one of the first and second plant-expressible genes encodes a desired polypeptide product selected from the group consisting of: selectable markers, toxins, hormones, proteases and viral proteins.

3. The nucleic acid according to claim 2, wherein the selectable marker confers antibiotic resistance, herbicide resistance, color change, or encodes a polypeptide which can react with a compound to produce a detectable signal.

4. A nucleic acid sequence according to claim 1, characterized in that the transcriptional promoter is constitutive or inducible plant specific promoter.

5. The nucleic acid according to claim 4, wherein the inducible promoter is activated by environmental conditions, by a pathogen, or by chemicals aimed at plant protection.

6. The nucleic acid according to claim 1, additionally comprising in the 3' position of the $IRES_{MP}$ an IRES, which may be the same as or different from the $IRES_{MP}$ and a gene encoding a desired polypeptide selected from the group consisting of selectable markers, toxins, hormones, proteases and viral proteins to produce a multicistronic gene transcript.

7. The nucleic acid according to claim 1 or 6, wherein the bicistronicor multicistronic gene transcript provides for coordinated expression of multiple polypeptides to produce an enzyme or several enzymes of a biosynthetic pathway.

8. The nucleic acid according to claim 6, wherein the selectable marker confers antibiotic resistance, herbicide resistance, color change, or encodes a polypeptide which can react with a compound to produce a detectable signal.

9. A eukaryotic cell transformed with an nucleic acid sequence according to claim 1.

10. A transgenic plant containing a nucleic acid sequence according to claim 1.

* * * * *

UNITED STATES PATENT AND TRADEMARK OFFICE
CERTIFICATE OF CORRECTION

PATENT NO. : 6,376,745 B1  
DATED : April 23, 2002  
INVENTOR(S) : Joseph Atabekov et al.

It is certified that error appears in the above-identified patent and that said Letters Patent is hereby corrected as shown below:

<u>Title page,</u>  
Item [86], please change both the §371 Date and the §102(e) Date from "Feb. 8, 2000" to -- Dec. 16, 1999 --.

Signed and Sealed this

Fifteenth Day of April, 2003

JAMES E. ROGAN  
*Director of the United States Patent and Trademark Office*

SEQUENCE LISTING

<160> NUMBER OF SEQ ID NOS: 2

<210> SEQ ID NO 1
<211> LENGTH: 227
<212> TYPE: RNA
<213> ORGANISM: Crucifer tobamovirus

```
-continued

<400> SEQUENCE: 1
aucuaaguua gguuguaaac auauuagaga cguucuucau uugaagaguu acgcgagucu        60
ugugugaugu agcuaguaac cuaaauaauu gugcguauuu uucacaguua gaugagccgu       120
ugccgagguu cauaagaccg cgguaggcgg uguuugcuuu uuguaguaua auuaaauauu       180
ugucagauaa gagauuguuu agagauuugu ucuuuguuug auaaugu                    227

<210> SEQ ID NO 2
<211> LENGTH: 79
<212> TYPE: RNA
<213> ORGANISM: Crucifer tobamovirus

<400> SEQUENCE: 2
gggcgaauug gguaccgggc cccccucga ggucgacggu aucgauaccg ucgaccucga        60
gggggggccc gguaccaug                                                    79
```